United States Patent [19]

Alexander et al.

[11] Patent Number: 5,130,427
[45] Date of Patent: Jul. 14, 1992

[54] (2R)-2-[DI(2-PROPYL)PHOSPHONYLME-THOXY]-3-P-TOLUENESULFONYLOXY-1-TRIMETHYLACETOXYPROPANE, ITS PREPARATION AND USE

[75] Inventors: Petr Alexander; Antonin Holý; Hana Dvořáková, all of Prague, Czechoslovakia

[73] Assignee: Československá akademie ved, Prague, Czechoslovakia

[21] Appl. No.: 729,422

[22] Filed: Jul. 12, 1991

[30] Foreign Application Priority Data

Aug. 6, 1990 [CS] Czechoslovakia ............... 3871-90

[51] Int. Cl.$^5$ ............... C07F 9/6521; C07F 9/6509; C07F 9/6506; C07F 9/40
[52] U.S. Cl. ............................. 544/182; 544/243; 544/244; 546/23; 558/124; 558/179
[58] Field of Search ............... 558/179, 126, 124; 544/232, 243, 244, 182; 546/23

[56] References Cited

U.S. PATENT DOCUMENTS 4,968,686 11/1990 Townsend et al. ............... 514/258

FOREIGN PATENT DOCUMENTS 0270885 6/1988 European Pat. Off. ............... 544/232

OTHER PUBLICATIONS

Webb, R. R. et al. Tetrahedron Letters, vol. 29, pp. 5475–5478 (1988).

*Primary Examiner*—Mary C. Lee
*Assistant Examiner*—Michael G. Ambrose
*Attorney, Agent, or Firm*—Notaro & Michalos

[57] ABSTRACT

The invention relates to the new compound (2R)-2-[di(2-propyl)phosphonylmethoxy]-3-p-toluenesulfonyloxy-1-trimethylacetoxypropane and the method of producing it. The compound may be used for producing (S)-N-(3-hydroxy-2-phosphonylmethoxypropyl) derivatives of the heterocyclic purine and pyrimidine bases of antiviral activity.

5 Claims, No Drawings

(2R)-2-[DI(2-PROPYL)PHOSPHONYLMETHOXY]-3-P-TOLUENESULFONYLOXY-1-TRIMETHYLACETOXYPROPANE, ITS PREPARATION AND USE

The invention relates to (2R)-2-[di(2-propyl)phosphonylmetholy]-3-p-toluenesulfonyloxy-1-trimethylacetoxypropane, its producing and use in manufacturing antivirally active (S)-N(-3-hydroxy-2-phosphonylmethoxypropyl) derivatives of heterocyclic purine and pyrimidine bases.

Among compounds that are active against viruses inducing serious illnesses in man and in animals, the group of (S)-N-(3-hydroxy-2-phosphonylmethoxypropyl) derivatives of heterocyclic purine and pyrimidine bases (HPMP-derivatives) has an important position. So far, these compounds were prepared from (S)-N-(2,3-dihydroxypropyl) derivatives of purine and pyrimidine bases mainly by reaction of their 3'-O-chloromethylphosphonyl esters with aqueous solutions of alkali metal hydroxides (Czechoslovak Author's Certificate 233665) or from N,O$^3$-ditrityl derivatives by reaction with dialkyl p-toluenesulfonyloxymethanephosphonates or methanesulfonyloxymethanephosphonates (R. R. Webb, J. C. Martin: Tetrahedron Lett. 28, 4963 (1987)) in the presence of sodium hydride, followed by subsequent removal of the protecting groups by acidic or alkaline hydrolysis and finally with bromotrimethylsilane (Holý A., Rosenberg I., Dvořáková H.: Collect.Czech.Chem.-Commun. 54, 2470 (1989).

This procedure has a drawback in that it requires a prior preparation of the optically active (S)-N-(2,3-dihydroxypropyl) derivative (A. Holý: Collect.Czech.-Chem.Commun. 40, 187 (1975); Collect.Czech.Chem.-Commun. 43, 3103 (1978)) and in some cases its multistep protection (A. Holy, I. Rosenberg: Collect.Czech.-step protection (A. Holý, I Rosenberg: Collect.Czech.-H. Dvořáková: Collect. Czech.Chem.Commun. 54, 2470 (1989). Another possible approach consists in condensation of the heterocyclic base (its silyl derivative or alkali metal salt) with a suitable optically active organophosphorus synthon containing the preformed structure of the side-chain in the HPMP derivative. Such approach makes use of such protecting groups as e.g. benzyl which is stable during preparation of the synthon as well as during the condensation; however, this group requires a hydrogenolytical removal which in some cases destroys the heterocyclic base, decreases the yield and complicates the isolation of pure product (J. J. Bronson, I. Ghazzouli, M. J. M. Hitchcock, R. R. Webb, J. C. Martin: J.Med.Chem. 32, 1457 (1989)).

The said drawback is removed by the present invention related to (2R)-2-[di(2-propyl)phosphonylmethoxy]-3-p-toluenesulfonyloxy-1-trimethylacetoxypropane of the formula I

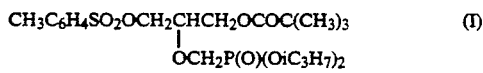

and the method of producing the same which consists in the reaction of (2R)-3-O-p-toluenesulfonyloxy-1,2-propandiol of the formula II

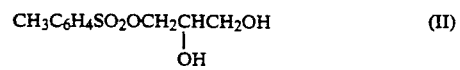

with an equimolar amount of N-trimethylacetylimidazole in an inert organic aprotic solvent, preferably dichloromethane, in the presence of a tertiary amine, preferably triethylamine, whereupon the obtained (2R)-3-p-toluenesulfonyloxy-1-trimethylacetoxy-2-propanol of the formula III

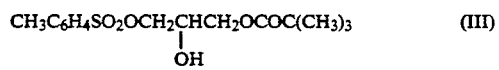

is reacted with dimethoxymethane and phosphorus pentoxide in an inert organic solvent, preferably dichloromethane and the (2R)-2-methoxymethoxy-3-p-toluenesulfonyloxy-1-trimethylacetoxypropane of the formula IV

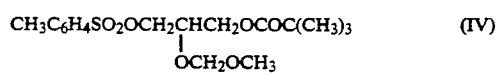

is treated with acetic anhydride in the presence of a Lewis acid, preferably boron trifluoride-diethylether complex at temperatures −5° C. to 5° C. and the obtained (2R)-2-acetoxymethoxy-3-p-toluenesulfonyloxy-1-trimethylacetoxypropane of the formula V

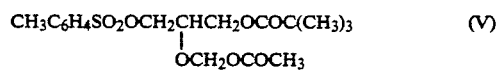

is heated with bromotrimethylsilane, preferably in toluene, at temperatures 100° C. to 120° C., the volatile components are evaporated in vacuo, the residue is heated with tri-(2-propyl) phosphite to 100°–200° C. and the product of the formula I is obtained by chromatography or molecular distillation.

The invention is further related to the method of utilization of the compound of the formula I for the production of (S)-N-(3-hydroxy-2-phosphonylmethoxypropyl) derivatives of the heterocyclic purine and pyrimidine bases of the general formula IV

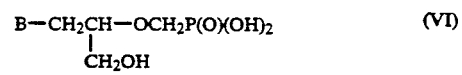

where B is purin-9-yl, purin-7-yl, pyrimidin-1-yl, pyrimidin-3-yl residue and their aza and deaza analogues consisting in the reaction of the compound of the formula I with sodium salt of the heterocyclic purine and pyrimidine base or its aza or deaza analogue, or with a mixture of such base and alkali carbonate, preferably sodium, potassium or cesium carbonate, in dimethylformamide at temperatures 60° C. to 120° C., whereupon the solvent is evaporated in vacuo and the mixture treated with sodium methoxide in methanol and subsequently with bromotrimethylsilane in an inert organic solvent, preferably in acetonitrile, and the product of the general formula VI is isolated by chromatography, preferably by ion-exchange chromatography.

The problem to be solved in designing an organophosphorus synthon suitable for the preparation of HPMP derivatives of the general formula VI consists in (a) the choice of a suitable reactive group capable of substituting the activated form of the heterocyclic base, (b) the choice of a suitable protecting group on the primary hydroxyl functionality that could be regiospecifically introduced, and after the reaction removed, without destroying the product of the formula IV, (c) the choice of suitable ester protecting groups on the phosphonic acid residue, (d) performing the whole synthetic sequence leading to the chiral synthon from an easily accessible chiral compound with retention of the optical purity of the synthon as well as the final product ((2S)-configuration), and (e) ability to perform the condensation of the synthon with the base and the whole subsequent work-up procedure both on a large scale and on a microscale under conditions suitable for preparation of radionuclide-labeled compounds.

As follows from the previous results, for the required N-substitution of heterocyclic bases it is advantageous to use chloro-, p-toluenesulfonyloxy or methanesulfonyloxy groups as reactive groups in the synthon I. The p-toluenesulfonyloxy derivatives are readily accessible from the alcohols and their purification is easy. Therefore, synthon I can be preferably prepared from the chiral (R)-3-p-toluenesulfonyloxy-1,2-propanediol of the formula II which is readily accessible from (R)-4-hydroxymethyl-2,2-dimethyl-1,3-dioxolane (2,3-O-isopropylidene-D-glycerol) by tosylation (A. Holý: Collect.Czech.Chem.Commun. 40, 187 (1975)) and subsequent acid hydrolysis.

This reaction may be performed using preferably an acid cation exchanger (e.g. Dowex 50 X 8) in the acid form which simplifies substantially the work-up procedure. Thus, e.g. a mixture of (R)-3-p-toluenesulfonyloxymethyl-2,2-dimethyl-1,3-dioxolane(50 g), Dowex 50 X 8 (H+-form, 10 g) and methanol (200 ml) is stirred at 60° C. for 7 h, the mixture is filtered, the solvent evaporated in vacuo, the residue is dissolved in chloroform, filtered through a column (100 ml) of silica gel, the filtrate is dried over magnesium sulfate, filtered and the solvent is evaporated at 40° C./2 kPa. The obtained sirupy (R)-3-p-toluenesulfonyloxy-1,2-propanediol(II) (41.4 g, 96%) is completely pure according to the thin-layer chromatography on silica gel in chloroform-methanol (19:1); $[\alpha]_D -10°$ (c=5.0, methanol).

The protecting group on the primary hydroxyl in the synthon must be stable under the conditions of the subsequent reaction sequence. These requirements are met by the trimethylacetyl group which can be removed only by methanolysis. The selective trimethylacetylation of compound II on the primary hydroxyl may be performed preferably with N-trimethylacetylimidazole, obtained by reaction of trimethylacetyl chloride with two equivalents of imidazole in chloroform. This product is stable enough to allow the removal of imidazole hydrochloride from chloroform solution by extraction with water. Thus, e.g., imidazole (13.6 g) is added to trimethylacetyl chloride (12.1 g) in chloroform (200 ml), the mixture is stirred at room temperature for 2 h, extracted with ice-cold water (3×50 ml), dried over magnesium sulfate and the chloroform is evaporated in vacuo, yielding N-trimethylacetylimidazole (14.1 g, 93%).

Compound II reacts with this imidazolide at room temperature in methylene chloride in the presence of triethylamine relatively slowly, but the reaction takes place selectively on the primary hydroxyl under formation of product III. Small amounts (<3%) of a side product (1,2-disubstituted derivative) can be easily removed by evaporation of the reaction mixture and chromatography of the residue on silica gel in chloroform. The reaction of compound II with trimethylacetyl chloride in the presence of triethylamine is much faster; however, even at 0° C. 6% of the 1,2-disubstituted compound and 2% of the undesired isomeric 2-O-trimethylacetyl derivative are formed.

The introduction of the phosphonylmethyl ether functionality on the 2-hydroxyl group in compound III was realized in an indirect way, starting from the key intermediate, 2-methoxymethyl ether of the formula IV. This is easily obtained from compound III by acid-catalyzed reacetalization with dimethoxymethane in the presence of phosphorus pentoxide. Although the reaction is heterogeneous, the product IV is obtained in high yield by chromatography of the organic (methylene chloride) phase.

The methoxymethyl group in compound IV reacts with acetic anhydride in the presence of a Lewis acid (e.g. boron trifluoride etherate) and the obtained acetoxymethyl derivative V is immediately converted into the reactive 2-bromomethyl ether by treatment with bromotrimethylsilane. This reaction proceeds slowly even at relatively high temperatures and its course should be monitored by thin-layer chromatography. The solvent and acetoxytrimethylsilane are evaporated in vacuo and the crude product is directly reacted with trialkyl phosphite, preferably with tri(2-propyl) phosphite. This phosphite is sufficiently reactive, 2-bromopropane formed in the reaction is volatile enough to be removed from the obtained product. The di(2-propyl) phosphonate group in the synthon of the formula I is not capable of alkylation of heterocyclic bases (as experienced with ethyl or particularly methyl esters). However, synthons analogous to that of the formula I with other ester functionalities, e.g. dimethyl, diethyl, di(2,2-dimethylpropyl), and other esters, can be prepared by analogous reaction with the corresponding trialkyl phosphite. The reaction is facile and, after its completion and evaporation of the volatile components, the final product (synthon I) is obtained by chromatography on silica gel.

All the steps of the reaction sequence leading to compound I proceed with high yields so that the total yield, related to the starting compound II, exceeds 40%. The reaction steps require no special reagents or equipment and the optical purity of the final product I is determined by the optical purity of compound II.

This is confirmed by the optical purity of known compounds of the formula VI which are prepared from the synthon I by condensation with sodium salt of the heterocyclic base. The reaction is carried out in dimethylformamide with suspension of the salt prepared in situ from the base and an equimolar amount of sodium hydride. The salt is then treated with an equimolar amount of compound I at 80°-100° C. under exclusion of moisture. In the case of pyrimidine derivatives, the most important thing is to ensure that the reaction takes place on N1; this is best achieved using 4-alkoxy-2-pyrimidinones. The formed N1-substituted derivatives may then be used in two ways: acid hydrolysis with aqueous mineral acid (or e.g. dilute acetic acid) affords derivatives of uracil or thymine, whereas ammonolysis, e.g. with alcoholic ammonia (or primary or secondary amines) at elevated temperatures in a pressure vessel smoothly affords derivatives of cytosine, 5-methylcytosine or their substituted analogs. In the purine series, the alkylation with compound of the formula I proceeds with some bases (e.g. adenine, 2,6-diaminopurine, 6-methylthiopurine, 3-deazaadenine) exclusively in the position N9, with other ones (hypoxanthine) in position N7, and still in other cases (e.g. guanine, 2-aminopurine, 1-deazaadenine) a mixture of N9 and N7-isomers is formed. In such cases it is necessary to use indirect methods based on an additional conversion of the heterocyclic base in compounds of the general formula VI or their precursors with modified bases, as in the preparation of the hypoxanthine or xanthine derivative by deamination of an adenine or guanine compound with nitrous acid or its esters, or in the synthesis of a 2-hydroxyadenine derivative by specific deamination of compound VI derived from 2,6-diaminopurine. The guanin-9-yl derivative and its N7-isomer are easily obtained by hydrolysis of compound prepared from 2-amino-6-chloropurine. The same intermediate may serve for the preparation of 2-amino-6-substituted derivatives; e.g. the derivative of 2,6-diaminopurine is obtained via the 2-amino-6-azidopurine derivative by hydrogenation.

The intermediate obtained by condensation of compound I with the base, is either isolated by chromatography and processed as described below, or the reaction mixture is directly methanolysed (with removal of trimethylacetyl group). This mixture is deionized on a column of a cation exchanger (e.g. Dowex 50) in a $H^+$-form, and the di(2-propyl) ester of compound VI is isolated; it is stable enough to withstand without decomposition washing out with dilute (1:10) aqueous ammonia from the ion exchanger.

After drying, the ester groups are removed by reaction with bromotrimethylsilane e.g. in acetonitrile, and after evaporation, hydrolysis of the residue and desalting, the pure product of the formula VI is isolated by preparative chromatography on a hydrophobized silica gel.

The optical purity of thus-prepared compounds of the formula VI is determined e.g. by HPLC in 4 mM $CuSO_4$ and 4 mM L-phenylalanine at pH 3.1. The above described procedure affords compounds VI of optical purity higher than 95%.

The invention is illustrated by examples of execution which by no means limit its scope.

EXAMPLE 1

Triethylamine (20 ml) is added to a solution of (2R)-3-O-p-toluenesulfonyloxy-1,2-propanediol (41.4 g, 168 mmol) and N-trimethylacetylimidazole (25.6 g) in dry dichloromethane (250 ml) and the mixture is allowed to stand for 7 days at room temperature until the starting compound disappears; the reaction is monitored by thin-layer chromatography on silica gel plates (TLC) in the system S1 (chloroform-methanol 95:5); $R_F=0.45$. Methanol (10 ml) is added, the solvent is evaporated in vacuo and the residue is dissolved in chloroform (50 ml) and filtered through a column of silica gel (400 ml) which is then washed with chloroform. Evaporation of the solvent and drying in vacuo afforded 48.3 g (146 mmol, 88%) of (2R)-3-O-p-toluenesulfonyloxy-1-trimethylacetoxy-2-propanol, $[\alpha]_D=-2.0°$ (c=0.5, chloroform). This product is dissolved in dichloromethane (300 ml), mixed with dimethoxymethane (25 ml) and phosphorus pentoxide (13 g, 90 mmol) is added under stirring and the stirring is continued for 30 minutes. The mixture is filtered through a layer of celite which is then washed with chloroform (200 ml), the filtrate is evaporated in vacuo, the residue is dissolved in chloroform (50 ml), the solution is filtered through a column of silica gel (200 ml) and eluted with chloroform. Yield 48.1 g (128.5 mmol, 88%) of (2R)-2-methoxymethoxy-3-O-p-toluenesulfonyloxy-1-trimethylacetoxy-2-propane, $[\alpha]_D=-2.0°$ (c=0.58, chloroform), TLC in S1, $R_F=0.70$. This product is mixed with acetic anhydride (17 ml), the mixture is cooled to 0° C. and boron trifluoride etherate (4.4 ml) is added. The mixture is stirred at 0° C. for 2 h, poured into a suspension of sodium hydrogen carbonate (20 g) in ice-cold water (100 ml), extracted with ether (3×30 ml), the combined extracts are washed successively with saturated solution of sodium hydrogen carbonate (20 ml) and water (20 ml) and dried over magnesium sulfate. The mixture is filtered, washed with ether (50 ml) and the filtrate is evaporated in vacuo, affording 49.7 g (123.5 mmol, 96%) (2R)-2-acetoxymethoxy-3-O-p-toluenesulfonyloxy-1-trimethylacetoxy-2-propane, $[\alpha]_D=-3,0°$ (c=0.47, chloroform). This product is mixed with toluene (100 ml) and bromotrimethylsilane (28.4 ml) and refluxed under argon (calcium chloride protecting tube) for 48 h (until the starting compound disappears; monitoring by TLC in the system S1). Then, the temperature is lowered to 40° C., the solvent is evaporated in vacuo and the residue is codistilled with toluene (50 ml) under argon. Tri(2-propyl) phosphite (30.8 ml) is added and the mixture is heated to 100° C. for 2 h with stirring. The reaction course is followed by TLC in chloroform (system S2). The mixture is evaporated in vacuo, the residue is codistilled with toluene (50 ml), dissolved in chloroform (50 ml), filtered through a column of silica gel (200 ml) and washed out with a gradient of ethyl acetate (up to 20%) in chloroform. Evaporation in vacuo and drying afforded 52 g (102 mmol, 83%) of (2R)-2-[di(2-propyl)phosphonylmethoxy]-3-O-p-toluenesulfonyloxy-1-trimethylacetoxypropane, $[\alpha]_D=-0.5°$ (c=0.40, chloroform).

EXAMPLE 2

A mixture of adenine (0.27 g, 2 mmol), sodium hydride (0.048 g) and dimethylformamide (5 ml) is heated to 80° C. for 1 h. A solution of (2R)-2-[di(2-propyl)phosphonylmethoxy]-3-O-p-toluenesulfonyloxy-1-trimethylacetoxypropane (1.16 g, 2 mmol) in dimethylformamide (5 ml) is added and the mixture is heated to 100° C. for 50 h. After evaporation in vacuo, the residue is purified by chromatography on silica gel in chloroform, containing an increasing concentration of methanol (the final concentration being 5% v/v). After evaporation of the solvent, the obtained product (TLC in S3, chloroform-methanol 4:1, $R_F=0.80$) is dissolved in methanol (5 ml) and stirred with 0.1 M methanolic sodium methoxide (2 ml) for 5 h. The mixture is neutralized by addition of a cation-exchanger (e.g. Dowex 50) in $H^+$-form, the suspension is applied onto the same ion-exchanger (20 ml), washed with water to drop of UV-absorption of the eluate (at 254 nm) to the original value and then the column is eluted with dilute (1:10, v/v) aqueous ammonia. The collected UV-absorbing eluate is concentrated, dried in vacuo and mixed with acetonitrile (8 ml) and bromotrimethylsilane (0.7 ml). After standing for 24 h at room temperature, the mixture is again evaporated and the residue is codistilled with acetonitrile (5 ml). The residue is allowed to stand with water (20 ml) and triethylamine (2 ml) for 30 minutes. After evaporation in vacuo, the residue is dissolved in water (10 ml) and applied onto a column of Dowex 50 in $H^+$-form (20 ml). The product is deionized as described above and the obtained crude residue (compound VI) is dissolved in water (10 ml), made alkaline with ammonia to pH 9–10 and applied onto a column (20 ml) of Dowex 1 X 2 in the acetate form. The column is washed with water to drop of UV absorption of the eluate (at 254 nm) to the original value and then the product is eluted with a linear gradient of acetic acid (to 0.5M, total volume 500 ml). The main UV-absorbing fraction is collected, the solvent is evaporated, the residue is codistilled with water and crystallized from water with addition of ethanol (5 vol. parts). The product is collected, washed with ethanol and ether and dried in vacuo; yield 0.55 g (64%) of 9-(S)-(2-phosphonylmethoxy-3-hydroxypropyl)adenine (free acid) which, according to HPLC analysis (vide supra) contains <4.5% of the (R)-enantiomer. $[\alpha]_D = -23.5°$ (c=5.1, 0.1M HCl). For $C_9H_{14}N_5O_5P.H_2O$ (321.2) calculated: 33.65% C, 5.02% H, 21.79% N, 9.65% P; found: 33.65% C, 4.96% H, 21.84% N, 9.79% P.

EXAMPLE 3

A mixture of 4-methoxy-2-pyrimidone (0.24 g), sodium hydride (48 mg) and dimethylformamide (5 ml) is heated to 80° C. for 1 h. A solution of (2R)-2-[di(2-propyl)phosphonylmethoxy]-3-O-p-toluenesulfonyloxy-1-trimethylacetoxypropane (1.16 g, 2 mmol) in dimethylformamide (5 ml) is added and the mixture is heated to 100° C. for 50 h. After evaporation in vacuo, the residue is purified by chromatography on silica gel in chloroform, containing an increasing concentration of methanol (the final concentration being 5% v/v). After evaporation, the product is dissolved in 30% methanolic ammonia (5 ml) and heated to 100° C. for 12 hours in a sealed ampoule. After evaporation in vacuo, the mixture is dried in vacuo, the residue is mixed with acetonitrile (8 ml) and bromotrimethylsilane (0.7 ml), allowed to stand at room temperature for 24 h and again evaporated. The residue is codistilled with acetonitrile (5 ml), mixed with water (20 ml) and triethylamine (2 ml) and set aside for 30 minutes. Further work-up is the same as described in Example 2. Yield, 0.22 g (37%) of 1-(S)-(2-phosphonylmethoxy-3-hydroxypropyl)cytosine (free acid); according to HPLC analysis (vide supra) the product contains less than 3% of the (R)-enantiomer. For $C_8H_{14}N_3O_6P.H_2O$ (297.3) calculated: 32.32% C, 5.43% H, 14.14% N, 10.44% P; found: 32.56% C, 4.96% H, 13.84% N, 10.37% P.

EXAMPLE 4

A mixture of cytosine (237.3 mg, 2.1 mmol), cesium carbonate (340 mg, 2.1 mmol) and dimethylformamide (6 ml) is stirred at 110° C. for 2 hours. A solution of (2R)-2-[di(2-propyl)phosphonylmethoxy]-3-O-p-toluenesulfonyloxy-1-trimethylacetoxypropane (1.16 g, 2 mmol) in dimethylformamide (5 ml) is added and the mixture is heated to 100° C. for 72 h. After evaporation in vacuo, the residue is purified by chromatography on silica gel in chloroform, containing increasing concentration of methanol (the final concentration being 5% v/v). After evaporation, the residue is purified by chromatography on silica gel in chloroform with a gradient of methanol. The further work-up procedure (reaction with bromotrimethylsilane, deionization and purification on anion exchanger) is the same as described in Example 2. Yield 0.33 g (52%) of 1-(S)-(2-phosphonylmethoxy-3-hydroxypropyl)cytosine (free acid, containing (HPLC analysis; vide supra) <1% of the (R)-enantiomer.

EXAMPLE 5

A mixture of 3-deazaadenine (1.3 g, 10 mmol), 60% dispersion of sodium hydride in paraffin (400 mg, 10 mmol) and dimethylformamide (35 ml) is stirred at 80° C. for 1 hour. After addition of (2R)-2-[di(2-propyl)phosphonylmethoxy]-3-O-p-toluenesulfonyloxy-1-trimethylacetoxypropane (5.6 g, 11 mmol) is added and the mixture is heated to 100° C. for 32 h. After evaporation in vacuo, the residue is codistilled with toluene (3×50 ml) in vacuo, the residue is adsorbed on silica gel (25 ml) and purified by chromatography on a column (100 ml) of silica gel in chloroform with a gradient of ethanol; the product is eluted with chloroform-ethanol 48:2. Yield 2.2 g (47%) of oily di(2-propyl) ester of 9-(S)-(2-phosphonylmethoxy-3-trimethylacetoxypropyl)-3-deazaadenine. This product is allowed to stand with 0.1M methanolic sodium methoxide (20 ml) at 20° C. for 20 h, the mixture is neutralized by addition of Dowex 50 X 8 (H+-form), the suspension is made alkaline with triethylamine, filtered, washed with methanol (200 ml) and the filtrate is evaporated in vacuo. Yield 1.78 g (4.6 mmol) of di(2-propyl) ester of 9-(S)-(2-phosphonylmethoxy-3-hydroxypropyl)-3-deazaadenine. This is mixed with acetonitrile (50 ml) and bromotrimethylsilane (5 ml) and set aside for 20 hours at 20° C. The mixture is again evaporated, the residue is codistilled with acetonitrile (3×25 ml), mixed with water (5o ml), triethylamine is added to pH 8 and the mixture is allowed to stand for 1 hour. After evaporation in vacuo, the residue is dissolved in water (20 ml) and applied onto a column of Dowex 50 X 8 in the H+-form (100 ml). The product is deionized as described in Example 2 and the obtained crude residue is dissolved in water, made alkaline to pH 9–10 with ammonia and this solution is applied onto a column (100 ml) of Dowex 1 X 2 in acetate form. The column is washed with water to drop of the UV absorption of the eluate (at 254 nm) to the original value and then the product is eluted with 0.5M acetic acid. The main UV-absorbing fraction is collected, the solvent is evaporated, the residue is codistilled with water and crystallized from water with addition of ethanol (5 vol. parts). The product is filtered, washed with ethanol and ether and dried in vacuo. Yield 0.56 g (41%) of 9-(S)-(2-phosphonylmethoxy-3-hydroxypropyl)-3-deazaadenine (free acid) containing (HPLC analysis) <4.5% of the (R)-enantiomer. $[\alpha]_D = -16.8°$ (c=0.5, 0.1M HCl). For $C_{10}H_{13}N_4O_5P.3H_2O$ (354.3) calculated: 15.80% N, 8.75% P; found: 14.71% N, 8.75% P. UV spectrum (pH 2): $\lambda_{max}$ 262 nm ($\epsilon_{max}$ 11600).

EXAMPLE 6

A mixture of 2-amino-6-chloropurine (1.0 g, 6 mmol), 60% dispersion of sodium hydride in paraffin (180 mg, 7.5 mmol) and dimethylformamide (35 ml) is stirred at 80° C. for 1 hour. After addition of (2R)-2-[di(2-propyl)phosphonylmethoxy]-3-O-p-toluenesulfonyloxy-1-trimethylacetoxypropane (2.5 g, 5 mmol) the mixture is heated to 80° C. for 20 h. After evaporation in vacuo, the residue is codistilled with toluene (3×50 ml) in vacuo, the residue is purified by chromatography on a column (100 ml) of silica gel in chloroform with a gradient of ethanol; the product is eluted with chloroform-ethanol 48:2. Yield 1.2 g of oily di(2-propyl) ester of 9-(S)-(2-phosphonylmethoxy-3-trimethylacetoxypropyl)-2-amino-6-chloropurine. This product is hydrogenated in 150 ml methanol and 0.5 ml concentrated hydrochloric acid over 10% palladium/charcoal catalyst (0.6 g) overnight. The suspension is filtered, alkalized by triethylamine and taken down to dryness. The residue is allowed to stand with 0.1M methanolic sodium methoxide (20 ml) at 20° C. for 20 h, the mixture is neutralized by addition of Dowex 50 X 8 (H+-form), the suspension is made alkaline with triethylamine, filtered, washed with methanol (200 ml) and the filtrate is evaporated in vacuo. The residue is deionized on a column (100 ml) of Dowex 50 X 8 (acid form) and further processed as described in Example 2. Ion-exchange chromatography and crystallization from water-ethanol afforded 9-(S)-(2-phosphonylmethoxy-3-hydroxypropyl)-2-aminopurine. Yield, 0.85 g (50%). For $C_9H_{14}N_5O_4P$ (287.2) calculated: 37,63% C, 4.91% H, 24.39% N, 10.80% P; found: 37,33% C, 5.07% H, 24.09% N, 10.70% P.

EXAMPLE 7

A mixture of 2-chloroadenine (10 mmol), cesium carbonate (2.3 g, 7.2 mmol) and (2R)-2-[di(2-propyl)-phosphonylmethoxy]-3-O-p-toluenesulfonyloxy-1-trimethylacetoxypropane (6.3 g, 12.4 mmol) in dimethylformamide (50 ml) is stirred under calcium chloride protecting tube for 4 h at 100° C. and further processed as described in Example 2. The ion-exchange chromatography and crystallization from water afforded 9-(S)-(2-phosphonylmethoxy-3-hydroxypropyl)-2-chloroadenine. Yield, 0.85 g (50%). For $C_9H_{13}ClN_5O_4P$ (321.7) calculated: 33,60% C, 4.07% H, 11.02% Cl, 21.77% N, 9.65% P; found: 33,41% C, 4.05% H, 10,78% Cl, 21.74% N, 10.03% P.

EXAMPLE 8

A mixture of 6-azacytosine (10 mmol), cesium carbonate (2.3 g, 7.2 mmol) and (2R)-2-[di(2-propyl)phosphonylmethoxy]-3-O-p-toluenesulfonyloxy-1-trimethylacetoxypropane (6.3 g, 12.4 mmol) in dimethylformamide (50 ml) is stirred under calcium chloride protecting tube for 12 h at 120° C. and further processed as described in Example 2. The ion-exchange chromatography and crystallization from water afforded 9-(S)-(2-phosphonylmethoxy-3-hydroxypropyl)-6-azacytosine. Yield, 1.7 g (60%). For (280.2) calculated: 30,00% C, 4.67% H, 20.00% N, 11.08% P; found: 29,85% C, 4.85% H, 20.29% N, 10.77% P.

EXAMPLE 9

A mixture of 1-deazaadenine (1.0 g, 7.5 mmol), 60% dispersion of sodium hydride in paraffin (300 mg, 7.5 mmol) and dimethylformamide (20 ml) is stirred at 80° C. for 1 hour. After addition of (2R)-2-[di(2-propyl)-phosphonylmethoxy]-3-O-p-toluenesulfonyloxy-1-trimethylacetoxypropane (4.2 g, 8.25 mmol) the mixture is heated to 100° C. for 8 h. After evaporation in vacuo, the residue is codistilled with toluene (3×50 ml) in vacuo, the residue is extracted by chloroform and purified by chromatography on a column (100 ml) of silica gel in chloroform with a gradient of ethanol; the product is eluted with chloroform-ethanol 46:4. Yield 1.5 g (42%) of oily di(2-propyl) ester of 9-(S)-(2-phosphonylmethoxy-3-trimethylacetoxypropyl)-1-deazaadenine. This product is allowed to stand with 0.1M methanolic sodium methoxide (20 ml) at 20° C. for 20 h, the mixture is neutralized by addition of Dowex 50 X 8 (H+-form), the suspension is made alkaline with triethylamine, filtered, washed with methanol (200 ml) and the filtrate is evaporated in vacuo. Yield 1.1 g (93 mmol) of di(2-propyl) ester of 9-(S)-(2-phosphonylmethoxy-3-hydroxypropyl)-1-deazaadenine. This is mixed with acetonitrile (40 ml) and bromotrimethylsilane (4 ml) and set aside for 20 hours at 20° C. The mixture is again evaporated, the residue is codistilled with acetonitrile (3×25 ml), mixed with water (50 ml), triethylamine is added to pH 8 and, the mixture is allowed to stand for 1 hour. After evaporation in vacuo, the residue is dissolved in water (20 ml) and applied onto a column of Dowex 50 X 8 in the H+-form (100 ml). The product is deionized as described in Example 2 and the obtained crude residue is dissolved in water, made alkaline to pH 9-10 with ammonia and this solution is applied onto a column (100 ml) of Dowex 1 X 2 in acetate form. The column is washed with water to drop of the UV absorption of the eluate (at 254 nm) to the original value and then the product is eluted with 0.5M acetic acid. The main UV-absorbing fraction is collected, the solvent is evaporated, the residue is codistilled with water add crystallized from water with addition of ethanol (5 vol. parts). The product is filtered, washed with ethanol and ether and dried in vacuo. Yield 0.6 g (62%) of 9-(S)-(2-phosphonylmethoxy-3-hydroxypropyl)-1-deazaadenine (free acid). For $C_{10}H_{15}N_4O_5P$ (302.2) calculated: 18.53% N, 10 28% P; found: 18.71% N, 10.04% P. UV spectrum (pH 2): $\lambda_{max}$ 281 nm; 260 nm ($\epsilon_{max}$ 17500; 3800).

EXAMPLE 10

A mixture of 8-azaadenine (0.95 g, 7 mmol), cesium carbonate 1.1 g, 3.5 mmol) and (2R)-2-[di(2-propyl)-phosphonylmethoxy]-3-O-p-toluenesulfonyloxy-1-trimethylacetoxypropane (4.1 g, 8 mmol) in dimethylformamide (45 ml) is stirred under calcium chloride protecting tube for 16 h at 120° C. and further processed as described in Example 2. After sodium methoxide treatment, the residue was chromatographed on silica gel (100 g) column to afford the 7- and 9-isomers of di(2-propyl) ester of 9-(S)-(2-phosphonylmethoxy-3-hydroxypropyl)-8-azaadenine. The residues are mixed with acetonitrile (25 ml) and bromotrimethylsilane (2.5 ml) and set aside for 20 hours at 20° C. The further work-up was performed as described in Example 2. Ion exchange chromatography and crystallization from water-ethanol-ether mixture afforded 9-(S)-(2-phosphonylmethoxy-3-hydroxypropyl)-8-azaadenine. Yield, 0.21 g (10%). For $C_8H_{13}N_6O_5P$ (304.2) calculated: 31,59% C, 4.31% H, 27.61% N, 10.19% P; found: 31,41% C, 4.05% H, 27.74% N, 10.03% P. UV spectrum (pH 2): $\lambda_{max}$ 264 nm ($\epsilon_{max}$ 8700). Similar work-up gave 7-(S)-(2-phosphonylmethoxy-3-hydroxypropyl)-8-azaadenine. Yield, 0.16 g (7.5%). For $C_8H_{13}N_6O_5P$ (304.2) calculated: 31,59% C, 4.31% H, 27.61% N, 10 19% P; found: 31,70% C, 4.08% H, 28.04% N, 10.33% P. UV spectrum (pH 2): $\epsilon_{max}$ 288 nm ($\epsilon_{max}$ 10500).

What we claim is:

1. (2R)-2-[Di(2-propyl)phosphonylmethoxy]-3-p-toluenesulfonyloxy-1-trimethylacetoxypropane of the formula I

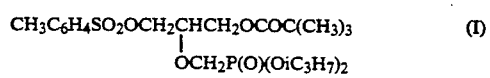

(I)

2. The method of producing the compound of the formula I in claim 1 consisting in the reaction of (2R)-3-O-p-toluenesulfonyloxy-1,2-propandiol of the formula II $$CH_3C_6H_4SO_2OCH_2CHCH_2OH \quad \text{(II)}$$
$$| \\ OH$$

with an equimolar amount of N-trimethylacetylimidazole in an inert organic aprotic solvent in the presence of a tertiary amine, whereupon the obtained (2R)-3-p-toluenesulfonyloxy-1-trimethylacetoxy-2-propanol of the formula III $$CH_3C_6H_4SO_2OCH_2CHCH_2OCOC(CH_3)_3 \quad \text{(III)}$$
$$| \\ OH$$

is reacted with dimethoxymethane and phosphorus pentoxide in an inert organic solvent and the (2R)-2-methoxymethoxy-3-p-toluenesulfonyloxy-1-trimethylacetoxypropane of the formula IV $$CH_3C_6H_4SO_2OCH_2CHCH_2OCOC(CH_3)_3 \quad \text{(IV)}$$
$$| \\ OCH_2OCH_3$$

is treated with acetic anhydride in the presence of a Lewis acid, at temperatures −5° C. to 5° C. and the obtained (2R)-2-acetoxymethoxy-3-p-toluenesulfonyloxy-1-trimethylacetoxypropane of the formula V $$CH_3C_6H_4SO_2OCH_2CHCH_2OCOC(CH_3)_3 \quad \text{(V)}$$
$$| \\ OCH_2OCOCH_3$$

is heated with bromotrimethylsilane at temperatures 100° C. to 120° C., the volatile components are evaporated in vacuo, the residue is heated with tri(2-propyl) phosphite to 100°–120° C. and the product of the formula I is obtained by chromatography or distillation.

3. The method of utilization of the compound of the formula I according to claim 1 for the production of (S)-N-(3-hydroxy-2-phosphonylmethoxypropyl) derivatives of the heterocyclic purine and pyrimidine bases of the general formula VI $$B-CH_2CH-OCH_2P(O)(OH)_2 \quad \text{(VI)}$$
$$| \\ CH_2OH$$

where B is a substituted purin-9-yl, purin-7-yl, or pyrimidin-1-yl, or pyrimidin-3-yl residue and their aza and deaza analogues consisting in the reaction of the compound of the formula I with a sodium salt of the heterocyclic purine or pyrimidine base or its aza or deaza analogue, or with a mixture of such base and alkali carbonate in dimethylformamide at temperatures 60° C. to 120° C., whereupon the solvent is evaporated in vacuo and the mixture treated with sodium methoxide in methanol and subsequently with bromotrimethylsilane in an inert organic solvent and the product of the general formula VI is isolated by chromatography.

4. A method according to claim 2, wherein the solvent is dichloromethane, the tertiary amine comprising triethylamine, the Lewis acid comprising boron trifluoridediethylether complex, the compound of formula V being heated in toluene.

5. A method according to claim 3, wherein the alkali carbonate comprises cesium carbonate, the inert inorganic solvent comprising acetonitrile, the chromatography being ion-exchange chromatography.

* * * * *